United States Patent
Schuldt-Hempe et al.

(10) Patent No.: US 6,966,918 B1
(45) Date of Patent: Nov. 22, 2005

(54) REINFORCED AREAL IMPLANT

(75) Inventors: Barbara Schuldt-Hempe, Rosenstr (DE); Christoph Walther, Dorfstr (DE)

(73) Assignee: Ethicon G.m.b.H. (DE)

( * ) Notice: Subject to any disclaimer, the term of this patent is extended or adjusted under 35 U.S.C. 154(b) by 0 days.

(21) Appl. No.: 10/070,219

(22) PCT Filed: May 26, 2000

(86) PCT No.: PCT/EP00/04817

§ 371 (c)(1), (2), (4) Date: Jul. 16, 2002

(87) PCT Pub. No.: WO01/15625

PCT Pub. Date: Mar. 8, 2001

(30) Foreign Application Priority Data

Aug. 31, 1999 (DE) .......................... 199 42 611

(51) Int. Cl.$^7$ ............................... A61B 17/08
(52) U.S. Cl. .................... 606/151; 623/11.11
(58) Field of Search .............. 602/44; 424/424, 424/425, 426; 606/213, 151; 623/13.18, 23.74–23.76, 11.11, 426, 1.5, 1.51, 1.54, 1.34, 1.4; 442/32, 44

(56) References Cited

U.S. PATENT DOCUMENTS

| | | | | |
|---|---|---|---|---|
| 3,769,144 A | * | 10/1973 | Economy et al. | 442/242 |
| 5,015,525 A | * | 5/1991 | Yagi et al. | 428/364 |
| 5,679,437 A | * | 10/1997 | Hackworth et al. | 428/143 |
| 5,876,452 A | * | 3/1999 | Athanasiou et al. | 623/23.72 |
| 5,935,878 A | * | 8/1999 | Glasser | 442/30 |
| 5,990,378 A | * | 11/1999 | Ellis | 623/11.11 |
| 6,013,853 A | * | 1/2000 | Athanasiou et al. | 424/423 |
| 6,090,996 A | * | 7/2000 | Li | 623/23.64 |
| 6,162,962 A | * | 12/2000 | Hinsch et al. | 623/11.11 |
| 6,174,279 B1 | * | 1/2001 | Girard | 600/37 |
| 6,281,262 B1 | * | 8/2001 | Shikinami | 523/105 |
| 6,319,264 B1 | * | 11/2001 | Tormala et al. | 606/151 |
| 6,355,065 B1 | * | 3/2002 | Gabbay | 623/11.11 |
| 6,528,437 B1 | * | 3/2003 | Hepfinger et al. | 442/38 |
| 2002/0133236 A1 | * | 9/2002 | Rousseau | 623/23.72 |
| 2003/0017771 A1 | * | 1/2003 | Kassner et al. | 442/48 |
| 2003/0040809 A1 | * | 2/2003 | Goldmann et al. | 606/151 |
| 2003/0045190 A1 | * | 3/2003 | Maguire | 442/6 |

FOREIGN PATENT DOCUMENTS

| | | |
|---|---|---|
| EP | 0797962 A2 | 10/1997 |
| WO | WO 9603091 A1 | 2/1996 |

* cited by examiner

Primary Examiner—Julian W. Woo

(57) ABSTRACT

A reinforced areal implant particularly suitable to the repair of inguinal hernias has a net-type basic structure with a pore size of 1.5 mm to 4.0 mm and comprises textile strengthening elements, whose bending resistance, measured in a three-point flexibility test at a support length of 20 mm, is in the range 0.015 N/mm to 0.4 N/mm. The basic structure preferably contains a non-absorbable material and additionally an absorbable multi-filament yarn.

10 Claims, 2 Drawing Sheets

REINFORCED AREAL IMPLANT

This application is a 371 of PCT/EP00/04817 filed on 26 May 2000, which in turn claims the priority of DE 199 42 611.2, filed on Aug. 31, 1999.

The invention concerns a reinforced areal implant, which can be used particularly for the repair of inguinal hernias.

From U.S. Pat. No. 2,671,444, a net-type surgical implant for the treatment of hernias is known. This implant is manufactured from polyethylene and can be cut to the required size by a surgeon. One disadvantage is that the implant is relatively stiff.

In order to improve the cloth-like quality of an implant net made from polypropylene or polyester for the treatment of hernias, it is proposed in DE 295 11 411 U1 to arrange attachments to the implant net, which are at least partially absorbable and which adhere to anatomical structures.

Furthermore, there are available implant nets made of polypropylene mono-filament which have a relatively great areal weight (implant mass) of 100 g/m$^2$ and a pore size of less than 1 mm. These implants nets are very stiff. Therefore, they are good for a laporoscopic application, as they unfold without difficulty, for example, but they do not match anatomical conditions in an optimal way. Thus, a cavity is readily formed, if these implants are used for the repair of inguinal hernias. Further disadvantages are the formation of a thick, strong scar plate and a disturbance of abdominal wall movement. Moreover, it is hard to see through such implant nets, which makes operations more difficult.

Conventional implant nets knitted from a composite material having an absorbable and a non-absorbable constituent are less stiff. Warp and pillar stitch are made of multi-filament yarns from non-absorbable polypropylene and an absorbable copolymer of L-lactide and glycolide in the ratio 10:90, which is marketed by the applicant under the designation "Vicryl". The areal weight amounts to about 56 g/m$^2$ with a polypropylene part of about 25 g/m$^2$. These implant nets fit the anatomical conditions well; they are soft and flexible and form no folds or cavities. Only a weak scar formation comes about, and the abdominal wall movement is not seriously disturbed. A pore size of about 2–4 mm provides good transparency. The reduced stiffness, however, brings disadvantages. For example, handling during care of an inguinal hernia is made more difficult. Such implant nets are ill-suited for laporoscopic use, as they are hard to unfold. In particular, a partial fold-out of the implant net against the spermatic cord can lead to problems.

The object of the invention is to provide an areal implant particularly suitable for repairing an inguinal hernia which on the one hand offers a good fit to anatomical conditions, but on the other hand is easily handled and can also be used for laporoscopic applications.

This problem is solved by a reinforced areal implant with the features of claim 1. Advantageous versions of the invention emerge from the sub-claims.

The reinforced areal implant according to the invention has a net-type basic structure with a pore size in the range 1.5 mm to 4.0 mm. It comprises textile strengthening elements whose bending resistance is in the range 0.015 N/mm to 0.4 N/mm. The bending resistance is given here with numerical values which can be determined in a three-point flexibility test in which the bending in the middle of a textile strengthening element is measured as a function of the force acting onto the middle of the textile strengthening element and perpendicularly to the textile strengthening element, where the (free) support length of the textile strengthening element is 20 mm. The numerical value given for the bending resistance in N/mm arises from the slope of this experimental curve in the region of smaller forces or bendings, where largely linear conditions dominate.

The net-type basic structure, at a pore size of 1.5 mm to 4.0 mm, is relatively coarse-mesh so that good transparency to the underlying tissue is possible, which facilitates surgery. The relatively large pores of the net-type basic structure also permit the entire implant mass being held low. The areal weight of the reinforced areal implants accoeding to the invention is preferably in the range 50 g/m$^2$ to 150 g/m$^2$. If the implant mass is low, after the surgery there are less foreign-matter reactions, and the implant heals in well, which again is assisted by the relatively large pores. On the other hand, the pores are sufficiently small for the net-type basic structure to accomplish the required support and holding function in the area of the surgery.

The textile strengthening elements have the effect that the reinforced areal implant according to the invention, as a whole, has an adequate stiffness for handling. It can therefore be well used in inguinal hernia repairs and also in laparoscopic applications. For example, the edges of the implant do not fold out, if the implant, starting at one of its edges, is cut, in order to lay it round the spermatic cord. On the other hand, the implant is not too stiff so that it fits to the anatomical conditions without folds or cavity formation and also does not essentially disturb the movability of the abdominal wall.

Preferably, the strengthening elements form a net-type strengthening structure with a pore size from 5 mm to 30 mm, this pore size preferably being several times the pore size of the basic structure. Such a coarse-mesh arrangement of the strengthening elements is sufficient to provide a sufficient stiffness of the implant.

In a preferred embodiment, the basic structure of the implant comprises a knitted fabric. Preferably, the strengthening elements are laid or knitted into the basic structure. In this case, the implant can be produced as a whole through a mesh-forming process. A possibility is the production with the aid of the multi-bar technology on crochet galloon machines or raschel machines.

Preferably, the basic structure comprises non-absorbable material (e.g. multi-filament yarn of polypropylene) or very slowly absorbed material (i.e. material that 180 days after the surgery still has at least 50% of its initial tear-strength), e.g. in a contribution with an areal weight in the range of 10 g/m$^2$ to 50 g/m$^2$. As this material is not absorbed or only slowly absorbed, the basic structure can assume the desired supporting and holding function in the patient's body permanently or at least for a very long period of time.

It is particularly advantageous, if additionally the basic structure has absorbable multi-filament yarn. For example, yarns of poly-p-dioxanone or yarns of a copolymer of L-lactide and glycolide (especially in the ratio 10:90, i.e. "Vicryl", or in the ratio 95:5) or mixtures of such yarns or multi-filament yarns are suitable. The absorbable yarns in the basic structure have the effect that the implant fits particularly well to local anatomical conditions and shows no folds or cavity formation on application. It is particularly helpful if a relatively large part of "Vicryl" multi-filament yarns is used. Fine "Vicryl" yarns are very quickly moistened by body fluids and therefore adhere to soft body tissue like fascia, muscles or the peritoneum much better than fabric structures from polypropylene multi-filament yarns or mono-filaments, which are very hydrophobic. With the aid of absorbable multi-filament yarns in the basic structure, it is thus possible for the implant in the operating area to fit very well and to attach to tissue, although it is relatively stiff as a whole, so as to improve handling.

For the strengthening elements, in particular pure mono-filaments, twisted mono-filaments, twisted or composite multi-filament yarns or mixtures thereof are suitable. The strengthening elements can be non-absorbable, partly absorbable, or completely absorbable. Suitable for strengthening elements are, for example, mono-filaments of polypropylene, multi-filament yarns of polypropylene, mono-filaments of poly-p-dioxanone, multi-filament yarns of a copolymer of L-lactide and glycolide in the ratio 10:90 ("Vicryl"), yarns of poly-p-dioxanone or mixtures thereof.

In a preferred embodiment of the invention, at least part of the strengthening elements has a color different from that of the basic structure. In this way, it is possible to provide the implant with a coarse-mesh colored grid, which makes it easier to a surgeon during surgery to assess any distortion of the implant. Preferably the color remains temporary only, i.e. after the surgery it fades. If the strengthening elements have several components, e.g., a mono-filament part or a multi-filament part of the strengthening elements can be colored.

Preferably, an implant provided for a surgical operation will be cut to size from areal material beforehand. But it is possible to use pre-made-up implants, for which, if required, the edge region can be secured against unravelling or reinforced. For the treatment of inguinal hernias, implants can be advantageous which have an aperture for the spermatic cord.

In the following, the invention is described more precisely by means of examples.

TABLE 1

Figure 1:
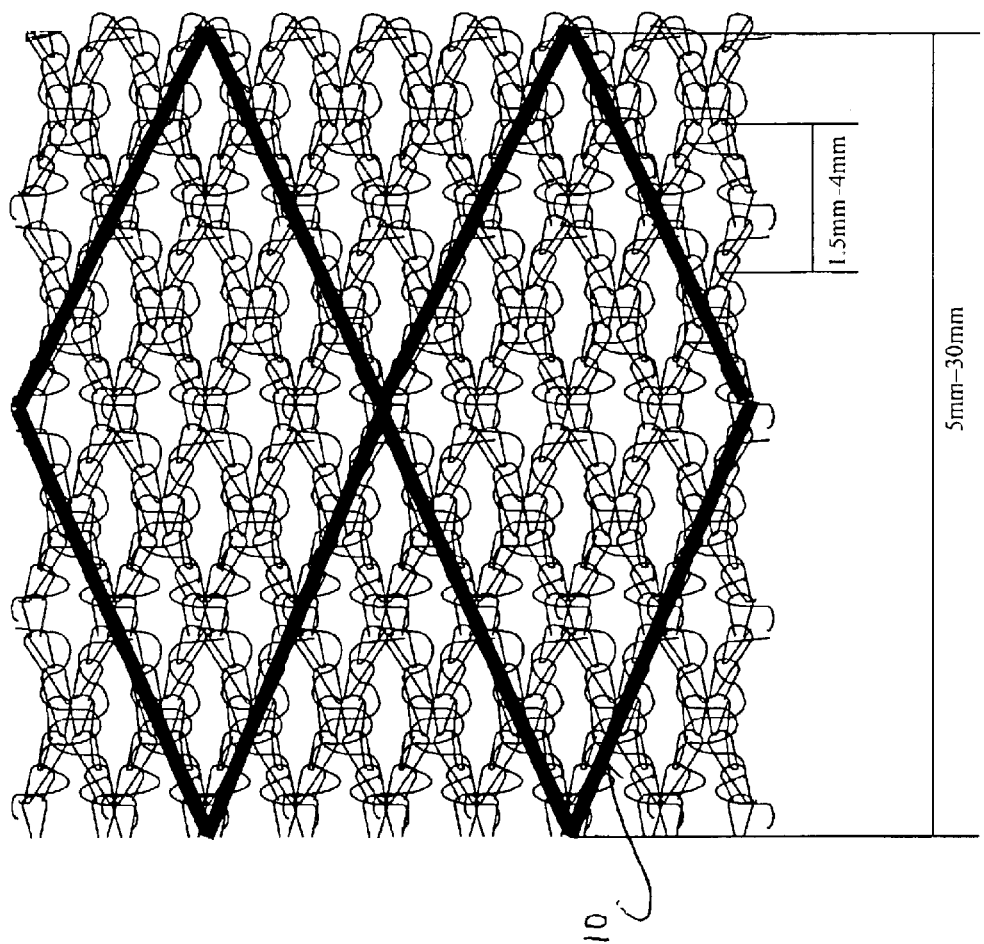
FIG. 1 is a depiction of the implant with pores and the textile strengthening elements 10.
Figure 2:
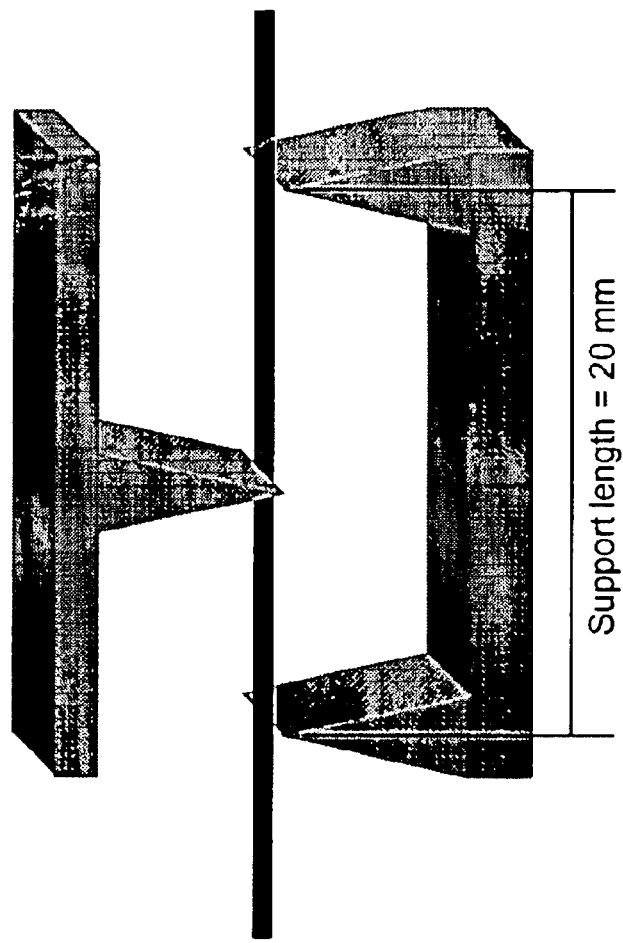
FIG. 2 illustrates the flexibility test referred to herein.

Thread system and material in the three embodiments according to model I, model II and model III

| No. | Thread System | Material |
|---|---|---|
| I | Warp: open pillar stitch | 1 × 60 den PP twine |
|   | Model shoot I + II: | Twist of 4 × 80 den "Vicryl" + |
|   | Basic knitting construction | 1 × 60 den PP |
|   | Rapport across 6 loops | |
|   | Model shoot III + IV: | Twist variant H |
|   | Pattern structure | Twist of 4 × 60 den PP, |
|   | Rapport across 24 loops | 2 × 80 den "Vicryl", violet and |
|   | | 1 × 6 mil PP mono-filament |
|   | | 1 × 4 fold twist + mono-filament |
| II | Warp: open pillar stitch | 1 × 60 den PP twine |
|   | Model shoot I + II: | Twist of 4 × 80 den "Vicryl" + |
|   | Basic knitting construction | 1 × 60 den PP |
|   | Rapport across 6 loops | |
|   | Model shoot III + IV: | Twist variant D |
|   | Pattern structure | Twist of 2 × 80 den "Vicryl", |
|   | Rapport across 36 loops | violet, and 4 × 60 den PP |
| III | Warp: open pillar stitch | 1 × 60 den PP twine |
|   | Model shoot I + II: | Twist of 4 × 80 den "Vicryl" + |
|   | Basic knitting construction | 1 × 60 den PP |
|   | Rapport across 6 loops | |
|   | Model shoot III + IV: | Twist variant I |
|   | Pattern structure | Twist of 4 × 60 den PP, |
|   | Rapport across 24 loops | 2 × 80 den "Vicryl", violet and |
|   | | 1 × 6 mil PP mono-filament |
|   | | 1 × 7 fold twist |

1 mil = 0.0254 mm; 1 den = 1 Denier

Further data for the thread systems and data concerning the material and kind of the yarns and filaments used are listed in Table 1 for these three embodiments. The strengthening elements "twist variant H" (model I), "twist variant D" (model II), and "twist variant I" (model III) are explained further below in more detail. In the case of all three embodiments, both the basic structure and the strengthening elements comprise absorbable and non-absorbable material, namely polypropylene (PP) as non-absorbable material and a copolymer of L-lactide and glycolide in the ratio 10:90 ("Vicryl") as absorbable material.

There follow some embodiments of strengthening elements which can be used in a reinforced areal implant. In the examples, in a way familiar to the expert, the materials and construction of the strengthening elements as well as their diameter and bending resistance are given. The latter is measured in a three-point flexibility test at a support length of 20 mm, as explained further above.

Example A

| | |
|---|---|
| Material: | Mixture of poly(vinylidene fluoride) and poly((vinylidene fluoride)-co-hexafluoropropylene) |
| Structure: | Mono-filament |
| Diameter: | 0.247 mm |
| Bending resist.: | 0.243 N/mm |

Example B

| | |
|---|---|
| Material: | PP multi-filament yarn (60 den) and violet "Vicryl" multi-filament yarn (80 den) |
| Structure: | 6 × 60 den PP and 2 × 80 den "Vicryl"; twist |
| Diameter: | 0.428 mm |
| Bending resist.: | 0.023 N/mm |

Example C

| | |
|---|---|
| Material: | PP mono-filament (thickness 6 mil) and violet "Vicryl" multi-filament yarn (80 den) |
| Structure: | 3 × 6 mil mono-filament and 2 × 80 den "Vicryl", violet |
| Diameter: | 0.328 mm |
| Bending resist.: | 0.147 N/mm |

Example D

| | |
|---|---|
| Material: | PP multi-filament yarn (60 den) and violet "Vicryl" multi-filament yarn (80 den) |
| Structure: | 4 × 60 den PP and 2 × 80 den "Vicryl", violet |
| Diameter: | 0.294 mm |
| Bending resist.: | 0.017 N/mm |

Example E

| | |
|---|---|
| Material: | PP multi-filament yarn (60 den) and violet "Vicryl" multi-filament yarn (80 den) |
| Structure: | 6 × 60 den PP yarn and 2 × 80 den "Vicryl" yarn as two-step twist: 1st step 1254 T/m, S-twist; 2nd step 465 T/m, Z-twist |
| Diameter: | 0.407 mm |
| Bending resist.: | 0.031 N/mm |

Example F

| | |
|---|---|
| Material: | PP multi-filament yarn (60 den) and violet "Vicryl" multi-filament yarn (80 den) |
| Structure: | 6 × 60 den PP yarn and 2 × 80 den "Vicryl" yarn as two-step twist: 1st step 1769 T/m, S-twist; 2nd step 695 T/m, Z-twist |
| Diameter: | 0.338 mm |
| Bending resist.: | 0.021 N/mm |

Example G

| | |
|---|---|
| Material: | PP multi-filament yarn (60 den) and violet "Vicryl" multi-filament yarn (80 den); plus PP mono-filament yarn |
| Structure: | 4 × 60 den PP yarn and 2 × 80 den "Vicryl" yarn and 1 × 6 mil-PP mono-filament als two-step twist: 1st step 1112 T/m, S-twist; 2nd step 413 T/m, Z-twist (1 × 7 twist) |

-continued

| | |
|---|---|
| Diameter: | 0.307 mm |
| Bending resist.: | 0.103 N/mm |
| Example H | |
| | |
| Material: | PP multi-filament yarn (60 den) and violet "Vicryl" multi-filament yarn (80 den); plus PP mono-filament yarn |
| Structure: | 4 × 60 den PP yarn, 2 × 80 den "Vicryl" yarn, violet, and 1 × 6 mil-PP mono-filament as two-step twist: 1st step 1112 T/m, S-twist; 2nd step 413 T/m, Z-twist; yarns shrunk in multiple-wound manner (4 + 1 twist) |
| Diameter: | 0.395 mm |
| Bending resist.: | 0.14 N/mm |
| Example I | |
| | |
| Material: | PP multi-filament yarn (60 den) and violet "Vicryl" multi-filament yarn (80 den); plus PP mono-filament yarn |
| Structure: | 4 × 60 den PP yarn, 4 × 80 den "Vicryl" yarn, violet and 1 × 6 mil-PP mono-filament as two-step twist: 1st step 1112 T/m, S-twist; 2nd step 413 T/m, Z-twist; yarns shrunk in multiple-wound manner (4 + 1 twist) |
| Diameter: | 0.37 mm |
| Bending resist.: | 0.1 N/mm |

The abbreviation PP, as well as the name "Vicryl" were already explained earlier. 1 mil=0.0254 mm; 1 den=1 Denier.

What is claimed is:

1. A reinforced areal implant, comprising a net-type basic structure having a pore size in the mange of 1.5 mm to 4.0 mm and textile strengthening elements whose bending resistance, measured in a three-point flexibility test at a support length of 20 mm, is in the range of 0.015 N/mm to 0.4 N/mm, where the textile strengthening elements form a net-type strengthening structure with a pore size in the range of 5 mm to 30 mm, said pore size being a multiple of the pore size of the basic structure.

2. The implant according to claim 1, wherein the basic structure comprises knitware.

3. The implant according to claim 2, wherein the strengthening elements are laid or knitted into the basic structure.

4. The implant according to claim 1, wherein the basic structure comprises non-absorbable material or very slowly absorbable material that retains at least 50% of its initial tear-strength after 180 days in-vivo.

5. The implant according to claim 4, wherein the basic structure comprises multi-filament yarn made of polypropylene.

6. The implant according to claim 1, wherein the basic structure comprises absorbable multi-filament yarn.

7. The implant according to claim 1, wherein the basic structure has at least one component selected from the group consisting of yarn of poly-p-dioxanone, yarn of a copolymer of L-lactide and glycolide in the ratio of 10:90, yarn of a copolymer of L-lactide and glycolide in the ratio of 95:5, yarn of a copolymer of L-lactide and glycolide in a different ratio.

8. The implant according to claim 1, wherein the strengthening elements comprise at least one component selected from the group consisting of pure mono-filaments, twisted mono-filaments, twisted multi-filament yarns, and composite multi-filament yarns.

9. The implant according to claim 8, wherein the strengthening elements comprise at least one component selected from the group consisting of mono-filaments of polypropylene, multi-filament yarns of polypropylene, mono-filaments of poly-p-dioxanone, multi-filament yarns of a copolymer of L-lactide and glycolide in the ratio of 10:90, and yarns of poly-p-dioxanone.

10. The implant according to claim 1, wherein at least part of the strengthening elements has a color different from that of the basic structure.

* * * * *